Figure 1:
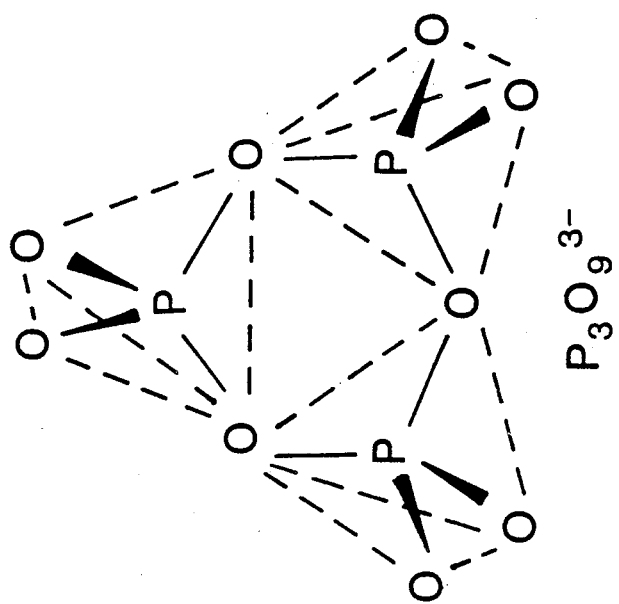
Figure 1:
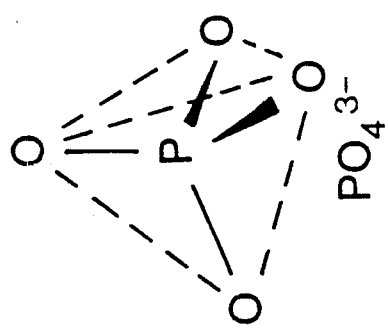
Figure 1:
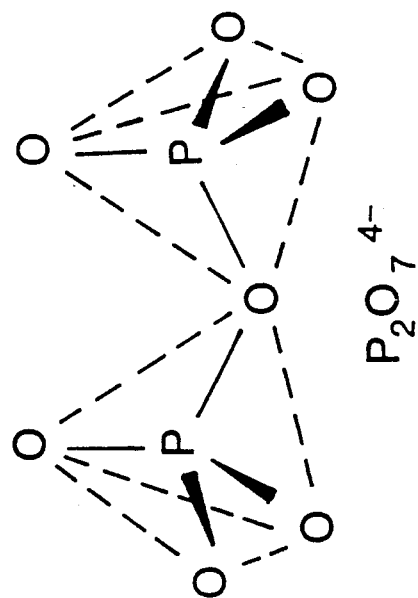

United States Patent [19]

Torstensson et al.

[11] Patent Number: 4,931,292
[45] Date of Patent: Jun. 5, 1990

[54] METHOD OF PREPARING IRON(III) PHOSPHATE COMPOUNDS FOR IRON FORTIFICATION OF FOOD PRODUCTS

[75] Inventors: Lars-Gunnar Torstensson, Kungälv; Per-Arne Dahlqvist, Svanesund; Malika Benjelloun, Göteborg, all of Sweden

[73] Assignee: EKA Nobel AB, Surte, Sweden

[21] Appl. No.: 138,379

[22] PCT Filed: Apr. 22, 1987

[86] PCT No.: PCT/SE87/00208

§ 371 Date: Dec. 22, 1987

§ 102(e) Date: Dec. 22, 1987

[87] PCT Pub. No.: WO87/06433

PCT Pub. Date: Nov. 5, 1987

[30] Foreign Application Priority Data

Apr. 23, 1986 [SE] Sweden ............................. 8601880

[51] Int. Cl.$^5$ ............................................. A23L 1/304
[52] U.S. Cl. ......................................... 426/2; 426/74; 426/648
[58] Field of Search ................. 426/74, 648, 649, 563, 426/547, 2; 424/147; 423/306, 307, 308, 314

[56] References Cited

U.S. PATENT DOCUMENTS

| | | | |
|---|---|---|---|
| 2,357,069 | 8/1944 | Barackman | 423/306 |
| 2,385,188 | 9/1945 | Booth | 423/306 |
| 2,550,491 | 4/1951 | McDonald | 426/563 |
| 3,803,292 | 4/1974 | Bell | |
| 3,876,813 | 4/1975 | Nimmo et al. | |

FOREIGN PATENT DOCUMENTS

| | | |
|---|---|---|
| 1044945 | 6/1975 | Canada . |
| 0061175 | 9/1982 | European Pat. Off. . |
| 1492692 | 10/1969 | Fed. Rep. of Germany . |
| 47-50000 | 12/1972 | Japan ................................. 423/306 |

OTHER PUBLICATIONS

Lauck 1969 Abstract of West German Patent Application No. 1,492,692.
Tucker 1959 Phosphates in Foods Cereal Science Today 4(4)91.
Cate 1959 Preparation of Crystalline Ferric Phosphates Soil Science 88(3)130–132.
Bridger et al., 1961 Metal Ammonium Phosphates as Fertilizers.
Salutsky 1964 Metal Potassium Phosphates J. Ag and Food Chemistry 12(6)486.
J. Janick 1972 Horticultural Science 2nd edition Freeman and Company San Francisco pp. 97–100.
*Nutrition Reports International,* May 1984, vol. 29, No. 5, K. Subba Rao et al., "Effect of Inorganic Polyphosphates on Dietary Iron . . . ," pp. 1101–1106.
*Handbook of Food Additives,* 2nd Ed., Edited by Thomas E. Furia, CRC Press, "Phosphates in Food Processing," pp. 759–761 and 763.
*The American Journal of Clinical Nutrition,* vol. 26, Aug. 1973, James D. Cook et al., "Absorption of Fortification Iron in Bread," pp. 861–871.
*Methods in Hematology,* Ed. by J. D. Cook, London: Churchill, 1980; Leif Hallberg, "Food Iron Absorption," pp. 116–133.
*The American Journal of Clinical Nutrition,* vol. 43, Jan. 1986, Leif Hallberg et al., "Low Bioavailability of Carbonyl Iron . . . ," pp. 59–67 and Figure.

*Primary Examiner*—Carolyn Paden
*Attorney, Agent, or Firm*—Burns, Doane, Swecker & Mathis

[57] ABSTRACT

Use of a certain type of complex iron(III)phosphate compounds for iron fortification of food products, in particular grain products. Especially flour and flour products, breakfast cereals, milk-based beverages, broths, rice and fermented food products, such as bread, are here concerned. The iron (III)phosphate compounds used have general formula $Z \cdot [FeM_{3y-3}(PO_4)_y] \cdot XH_2O$, wherein M is one of the ions $H^+$, $Na^+$, $K^+$, $NH_4^+$ or a combination thereof, $1.5 \leq y \leq 3.0$, $X \geq 0$ and Z is an integer from 1 and upwards, Z · y being an integer. A preferred embodiment is the use oy being an integer. A preferred embodiment is the use of a compound having the formula $Fe_3H_8(NH_4)(PO_4)_6 \cdot 6H_2O$. The invention also relates to a method preparing iron-fortified food products and further to the iron-fortified food products.

12 Claims, 6 Drawing Sheets $P_3O_9^{3-}$ $PO_4^{3-}$ $P_2O_7^{4-}$

Fe  P  O

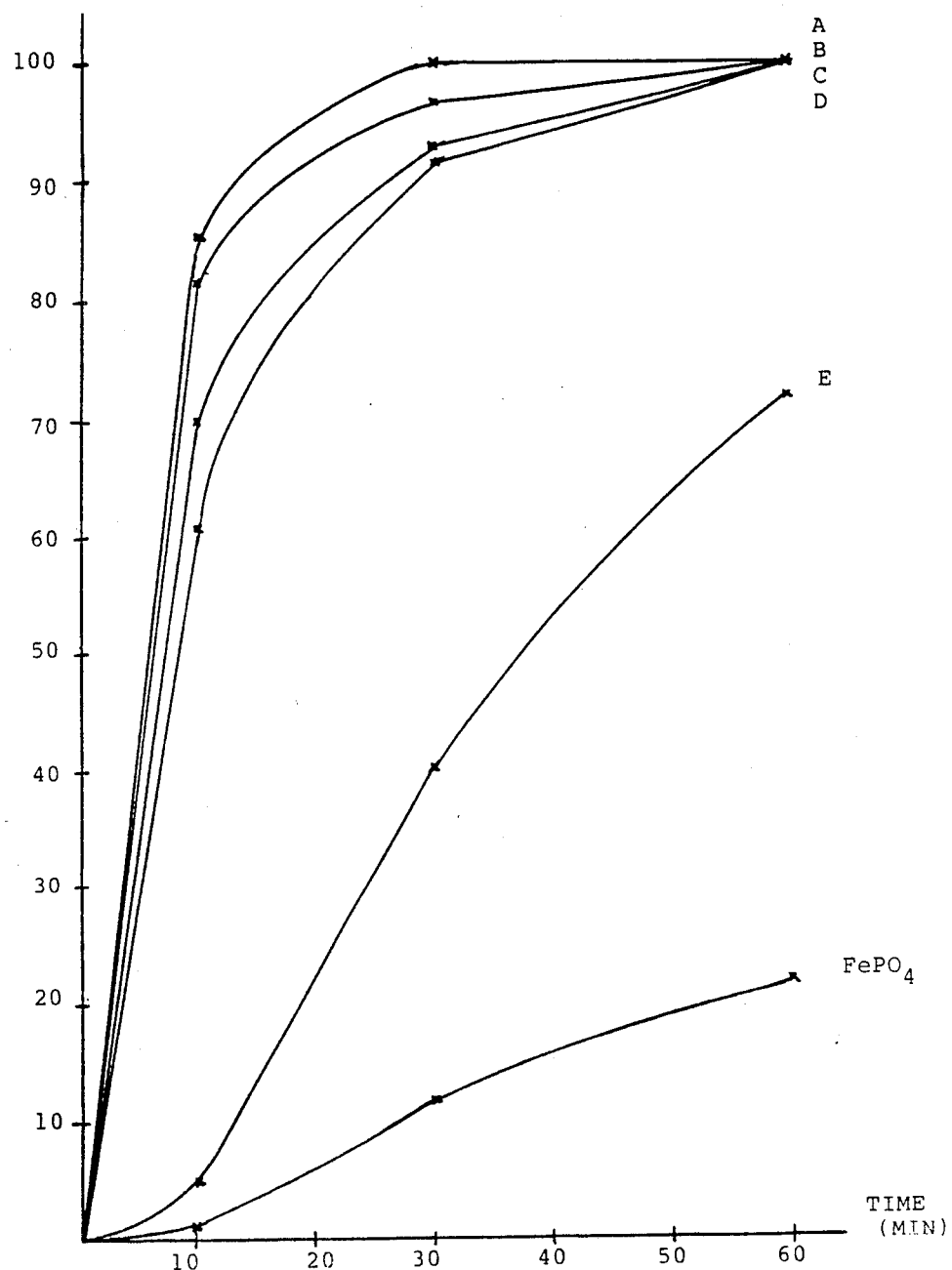

METHOD OF PREPARING IRON(III) PHOSPHATE COMPOUNDS FOR IRON FORTIFICATION OF FOOD PRODUCTS

TECHNICAL FIELD OF THE INVENTION

The present invention relates to the use of special iron(III)phosphates for iron fortification of food products, in particular grain products. Especially flour and flour products, breakfast cereals, milk-based beverages, broths, rice and fermented food products, such as bread, are here concerned.

BACKGROUND OF THE INVENTION

Internationally seen, iron deficiency is one of the most frequent deficiency diseases which occurs in most developing countries and is also the main deficiency disease in industrial countries. Above all, iron deficiency condition is a problem to women of fertile age but is also to be found in children and young people.

Iron fortification of certain food products is one way to prevent the occurrence of iron deficiency. Since grain products are an important source of consumer goods and are relatively cheap, they are usually chosen as carriers of iron additives.

A suitable iron-fortifying agent must satisfy a number of requirements. First, it must be innocuous to the human body. Furthermore, it must be water-insoluble in neutral or moderately acid environment, which is decisive of good storage properties. It must further have high absorbability in the human body, i.e. good bioavailability, which means good solubility in the gastrointestinal tract at a pH value of about 1 (corresponding to 0.1M HCl). It must also be chemically definable and producible in a reproducible way, i.e. it must have guaranteed constant and controllable properties.

Examples of substances used as iron-fortifying agents are iron powder (reduced iron), iron (III)phosphate iron (III) diphosphate, iron (III) sodium disphosphate, iron(II)sulphate and soluble organic iron(II)compounds. Soluble iron(II)compounds (e.g. iron(II)sulphate) have high bioavailability in the human body. Being easily soluble, they suffer, however, from the disadvantages of causing discolouration and changes in taste of the fortified products when they react with other components in the food, whereby coloured complex compounds and oxidation products are formed which turn the food product rancid. Iron sources which are water-insoluble (e.g. iron powder, iron(III)phosphate) are relatively inert and do not affect the food product to any appreciable extent. The lower solubility in water of these substances is, however, usually associated with low solubility at low pH and thus gives lower bioavailability as compared with soluble iron salts. To date, it has not been possible to find an iron-fortifying agent which in a favourable way combines the requirements for low solubility in water and solubility in the gastrointestinal tract (i.e. at low pH), respectively.

For iron fortification of flour and flour products, reference is made to, for example, U.S. Pat. No. 3,803,292 which describes iron fortification of flour by using a combined iron(II)sulphate preparation. It appears that one has managed to combine the high bioavailability of iron (II)sulphate with long storage life which has been obtained by the use of particles of iron-(II)sulphate monohydrate having a surface coating of iron(II)sulphate heptahydrate. However, no bioavailability tests have been accounted for, only stability tests.

Furthermore, Canadian patent specification No. 1,044,945 describes an iron-fortified fruit porridge powder for infants, in which the fortification iron is electrolytic iron (iron powder having a small particle size). No bioavailability tests have been accounted for.

Reference is also made to U.S. Pat. No. 3,876,813 which describes the bioavailability advantage of iron-(III)polyphosphate as compared with iron(II)sulphate. These results are, however, not relevant to use on humans since they are based on animal (rat) experiments only. Iron absorption in animals, such as for example rats, is about 100 times higher than in humans, calculated per unit of weight, and furthermore there are considerable distinctions with regard to the capability of absorbing different iron compounds. Thus, studies of bioavailability in humans are required in order to reach a relevant assessment.

The "Handbook of Food Additives", 2 Ed., T. E. Furia, Cleveland, Ohio (1972), p. 660, states that, inter alia, iron(III)orthophosphate and sodium iron pyrophosphate do not, in connection with the fortification of food products, cause the food product to turn rancid, but that their value as fortifying agents is questionable in respect to the bioavailability of iron.

Moreover, a paper by S. Rao and N. Rao, Nutrition Reports International, Vol. 29, No. 5, 1984, pp. 1101–1106, describes the fortification of food products by sodium tripolyphosphate which by chelate bonding with iron can increase iron absorption in the human body.

A comparative study of bioavailability in humans has been carried out with regard to the commercially most frequent iron-fortifying agents which comprise iron(II)-sulphate, iron powder and iron(III)phosphate, see Cook et al, "Absorption of fortification iron in bread" in the American Journal of Clinical Nutrition 26, pp. 861–872, August 1973, according to which iron(II)sulphate is considered to have the highest absorbability (p. 864, col. 2, first complete par.). For these comparisons, an isotope measuring technique was used for measuring the absorption of the thus marked fortification iron in the human body, a technique subsequently described in greater detail by Hallberg, "Food Iron Absorption", Methods in Hematology, 1980, pp. 116–133, and by Hallberg et al., "Low bioavailability of carbonyl iron in man: studies on iron fortification of wheat flour", the American Journal of Clinical Nutrition 43, pp. 59–67, January 1986. This technique will be described in greater detail in the Examples below.

THE PROBLEM

Within the art, there is thus the problem of finding an iron-fortifying agent for food products, which both has high bioavailability in humans and insignificantly affects the appearance, the taste and the keeping qualities of the fortified food product. Thus, the desired agent shall be water-insoluble such that the food product is not discoloured and does not turn rancid, but shall still have sufficient solubility in the gastrointestinal contents so as to give good bioavailability. The common commercially used iron compounds have appeared to be either sufficiently soluble in water to cause technical problems or so difficult to dissolve that the absorbability in the human body is low.

SOLUTION OF THE PROBLEM

It has been found that common iron(III)phosphate compounds which are commercially used to date, have very low solubility at pH 1. By "common" are here meant the iron(III)phosphates which are stated in the Food Chemicals Codex, FCC, to be commercially used for fortification purposes.

We have now found that complex iron(III)phosphate compounds which include monovalent cations, have higher solubility at pH 1. The solubility has been increased in that $NH_4^+$, $H^+$ and/or $Na^+$ and $K^+$ have been added to the iron(III)orthophosphate. These compounds are comprised by the denomination iron(III)phosphates, but they distinguish from the common iron(III)phosphates stated in the FCC, $FePO_4 \times XH_2O$, mainly owing to a different mole fraction between phosphate and iron, which affects the solubility. Having made extensive systematic studies, we have further found a special type of complex iron(III) phosphate compound having a well-defined X-ray crystallographic structure. Unexpectedly, this type has very good properties with respect to solubility at pH 1. Its bioavailability, particularly in flour products, also appeared to be unexpectedly high, simultaneously as it has the same favourable properties as pure iron(III)phosphate compounds in respect of suitability as an ironfortifying agent, i.e. it is almost colourless and has low reactivity in food products.

The invention thus relates to the use of complex iron(III)phosphate compounds for iron fortification of food products, the compounds used having the formula

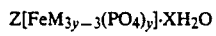

$$Z[FeM_{3y-3}(PO_4)_y] \cdot XH_2O$$

wherein M is one of the the ions $H^+$, $Na^+$, $K^+$, $NH_4^+$ or a combination thereof, $1.5 \leq y \leq 3.0$, $X \geq 0$ and Z is an integer from 1 and upwards, $Z \cdot y$ being an integer. Preferably, Z is an integer from 1 to 5.

If the chemical formula of the iron(III)phosphate compounds used according to the present invention is written such that merely one iron atom is included per unit of formula, it may be written

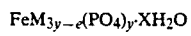

$$FeM_{3y-c}(PO_4)_y \cdot XH_2O$$

The invention also relates to a method of preparing iron-fortified food products and further to the iron-fortified food products.

The solubility of the iron(III)phosphates which are used according to the invention, has been increased in that the mole fraction between phosphate and iron has been increased. As a compensation for the increased negative charge, the compound thus comprises also monovalent cations.

The compounds mentioned above are per se known from, inter alia, J. F. Haseman, J. R. Lehr and J. P. Smith, Mineralogical Character of some iron and aluminium phosphates containing potassium and ammonium, Soil Science Society Proceedings 15(1951), pp. 76-84. The above compounds distinguish from iron(III)orthophosphates, -diphosphates and -polyphosphates which are previously known in connection with fortification, by having a completely different structural composition.

Iron phosphates are composed of iron ions, divalent or trivalent, and phosphate ions. The phosphate ions and also the bonding between the phosphate ions and the iron ion can be very different in character. The most frequent type of iron phosphate is iron orthophosphate. These phosphates contain the group $PO_4^{3-}$, as a discrete unit. Typical compounds of this type are $FePO_4 \cdot 2H_2O$ which as a mineral is called strengite, or $Fe_3(PO_4)_2 \cdot 8 H_2O$ which as a mineral is called vivianite.

The diphosphates or pyrophosphates contain a group $P_2O_7^{4-}$ in which two phosphate tetrahedrons share a corner. An iron(III)diphosphate has the formula $Fe_4(P_2O_7)_3 \cdot 9 H_2O$.

The polyphosphates comprise chains or rings of $PO_4$ tetrahedrons. The chain length may vary most considerably. As a rule, the compounds are non-crystalline and are composed in various manners. The polyphosphates form strong bonds with iron(III)ions.

Complex iron phosphates contain, in addition to iron, also other cations. The compounds used according to the present invention are composed of orthophosphates and contain one or more of the cations $H^+$, $Na^+$, $K^+$ and $NH_4^+$. In common iron phosphate, all oxygen atoms in the orthophosphate groups are bonded with iron, whereas the complex iron phosphates contain oxygen atoms which are not bonded with iron. If the compound contains $H^+$ ions, they are bonded with these oxygen atoms. Since the complex phosphates contain other cations than iron, the mole fraction between phosphate and iron is larger than in a pure iron phosphate. The mole fraction between phosphate and iron as well as the composition of the remaining cations are very important to the chemical properties of the compounds.

Figure 2:
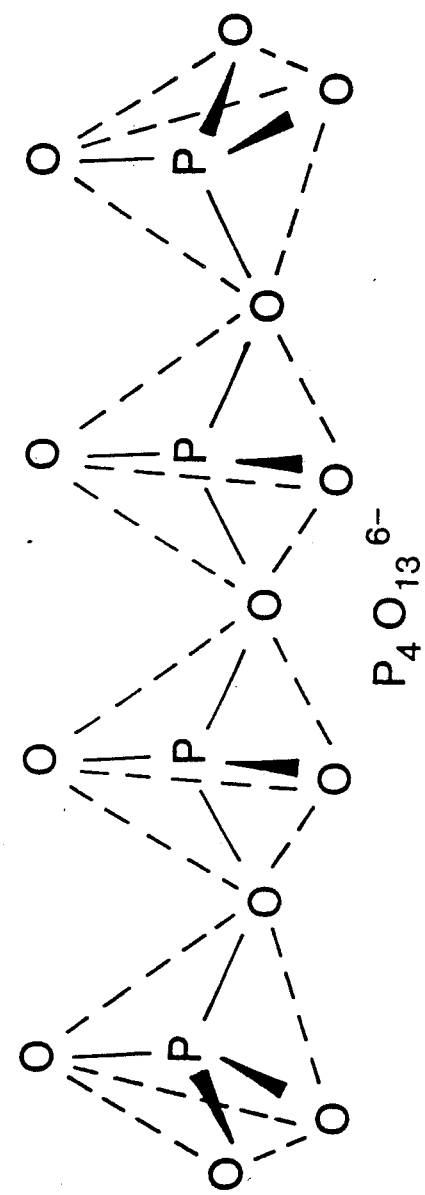
Figure 3:
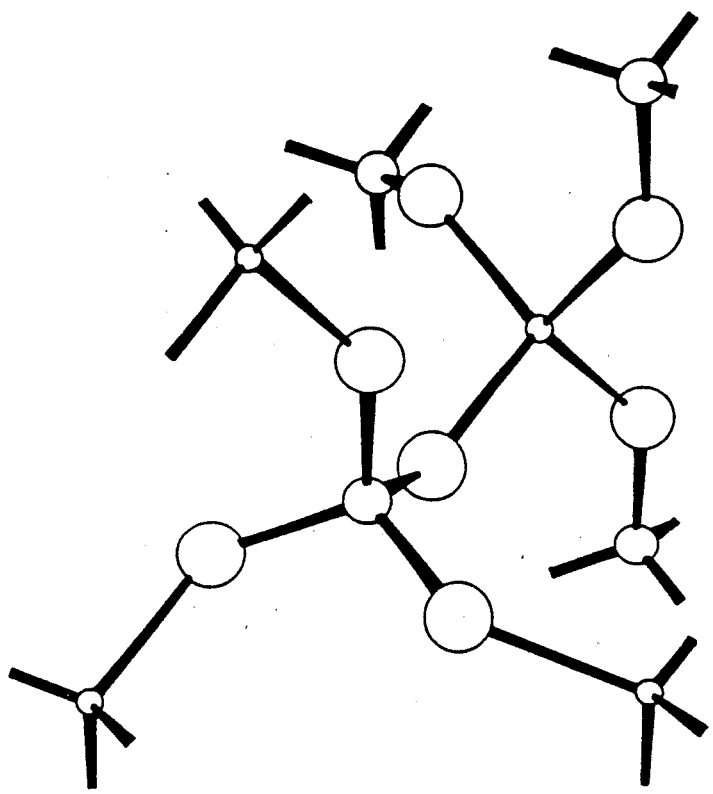
Figure 3:
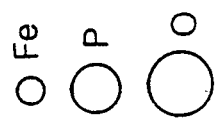
Figure 4:
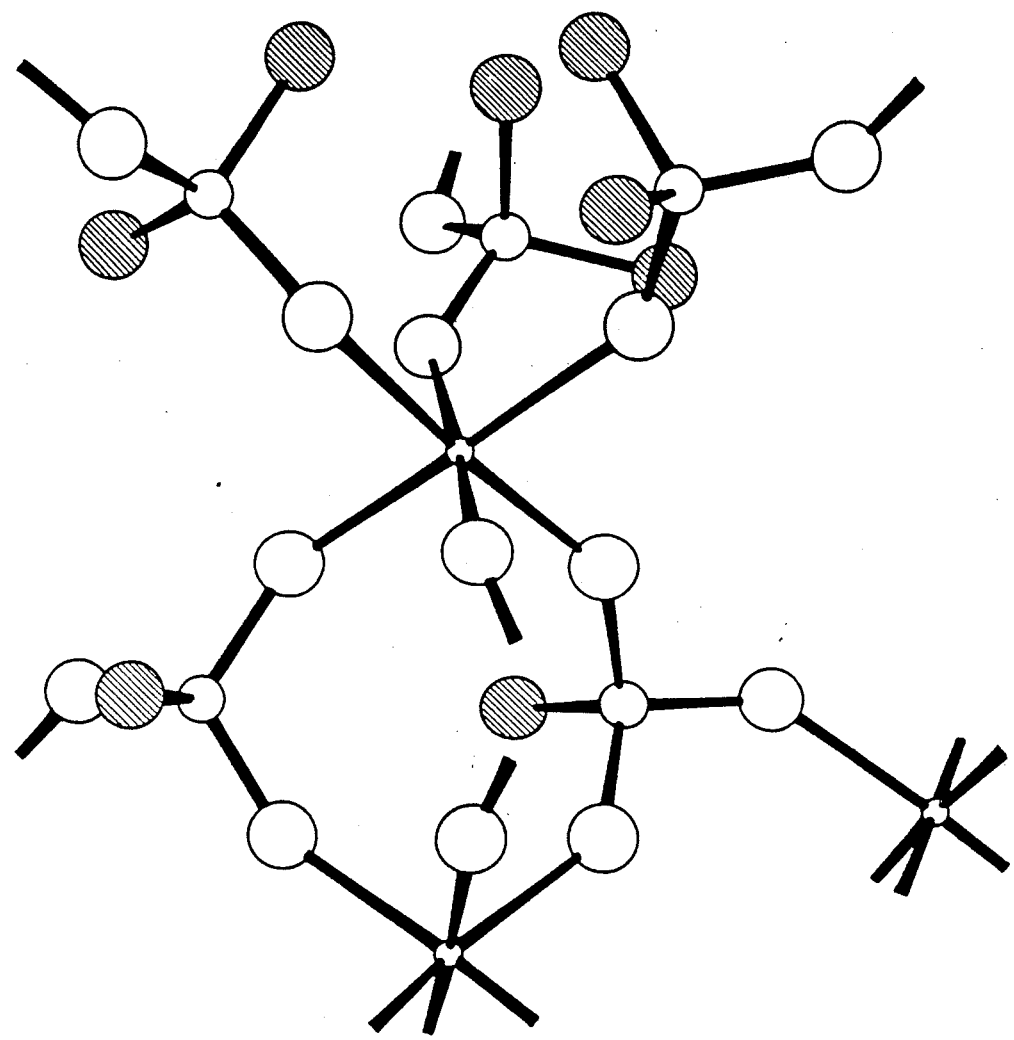
Figure 4:
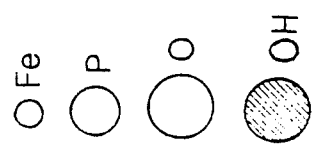

FIGS. 1 and 2 show different spatial arrangements for different types of phosphate ions which are all based on a tetrahedron unit. FIGS. 3 and 4 show atomic models for a common phosphate compound and a compound according to the invention having such phosphate ion tetrahedrons inserted in the space lattice.

It will be appreciated from FIGS. 3 and 4 that the complex compounds according to the invention distinguish materially from common phosphates which are previously known in connection with fortification.

A large number of substances having the above-mentioned general formula may be prepared (see the Table below). Their solubility and stability properties are, to a certain extent, affected by the value of y and by the composition of the cations in the structure. Most of the compounds are very stable at room temperature and are not hygroscopic.

TABLE

Examples of compounds according to the present invention

| | | |
|---|---|---|
| $y = 1.5$; | $Z = 2$ | $Fe_2Na_3(PO_4)_3 \cdot 3 H_2O$, $Fe_2Na_3(PO_4)_3 \cdot 4 H_2O$ |
| $y = 1.8$; | $Z = 5$ | $Fe_5H_8Na_4(PO_4)_9 \cdot 10 H_2O$ |
| $y = 2.0$; | $Z = 1$ | $FeH_3(PO_4)_2 \cdot 2 H_2O$ |
| | | $FeH_2Na(PO_4)_2$ |
| | | $FeH_2Na(PO_4)_2 \cdot 0.5 H_2O$ |
| | | $FeH_2Na(PO_4)_2 \cdot H_2O$ |
| | | $FeH_2Na(PO_4)_2 \cdot 3 H_2O$ |
| | | $FeNa_3(PO_4)_2 \cdot H_2O$ |
| | $Z = 3$ | $Fe_3H_8K(PO_4)_6 \cdot 6 H_2O$ |
| | $Z = 1$ | $FeH_2K(PO_4)_2$ |
| | | $FeH_2K(PO_4)_2 \cdot H_2O$ |
| | $Z = 3$ | $Fe_3H_8(NH_4)(PO_4)_6 \cdot 6 H_2O$ |
| | $Z = 1$ | $FeH_2(NH_4)(PO_4)_2$ |
| | | $FeH_2(NH_4)(PO_4)_2 \cdot 0.5 H_2O$ |
| $y = 2.67$; | $Z = 3$ | $Fe_3H_{14}K(PO_4)_8 \cdot 4 H_2O$ |
| $y = 3.0$; | $Z = 1$ | $FeH_6(PO_4)_3$ |
| | | $FeH_5Na(PO_4)_3 \cdot H_2O$ |
| | | $FeH_4Na_2(PO_4)_3 \cdot 3 H_2O$ |

All iron(III)phosphates in the Table are soluble in 0.1M HCl. The dissolving rate is affected more by the particle size than by the composition. Solubility examinations for representative compounds from the Table above are shown in the experimental part of the specification, and regarding the most preferred compounds, an extensive absorption and bioavailability test has also been carried out.

The compounds used according to the invention are prepared by reaction between iron(III)salts and $H_3PO_4$ in the presence of $NH_4^+$, $Na^+$ or $K^+$.

The iron(III)phosphates used according to the invention can be added as an iron-fortifying agent to e.g. flour in the usual manner, whereupon the flour can be used for baking bread. The fact that fortification and absorption results of equivalent values are obtained when the fortifying agent is used in non-fermented products has been shown in comparative tests where fortified flour has been made to porridge. In analysing the bioavailability in humans, use is made of radioactive iron labelling in the synthesis of the iron(III)compound used.

EXAMINATION OF BIOAVAILABILITY

The examination was carried out by the technique described in the above-mentioned paper by Hallberg et al.

The iron compound to be tested is labelled with radioactive iron, $^{55}Fe$, in the synthesis of the compound used. This iron is used to fortify flour from which buns are made by standard procedures, for example as follows:

| Ingredients | Parts by weight |
|---|---|
| wheat-flour | 100 |
| sugar | 3.5 |
| salt | 1.0 |
| yeast | 6.5 |
| water | 83 |
| iron source | $6.5 \cdot 10^{-3}$ |

The iron occurring naturally (native iron) in wheat-flour is labelled by adding tracer amounts of $^{59}Fe$-labelled iron(III)chloride. The buns are thus made of flour which is labelled with two different radioactive isotopes.

The ingredients are mixed, and the dough is allowed to rise for 30 minutes. After the usual kneading, the dough is placed in small aluminium baking tins where the dough pieces are allowed to rise for another 30 minutes. The dough pieces in the baking tins are subsequently baked at a temperature of 250° C. for 10 minutes These double-labelled buns are served a group of test subjects, for breakfast with coffee, margarine and marmalade two successive mornings after a night's fast. No food or beverage is allowed for three hours after breakfast. Two weeks after the last breakfast, blood tests are made to measure the occurrence of $^{55}Fe$ and $^{59}Fe$ in blood. Furthermore, the totally absorbed amount of $^{59}Fe$ in the body is measured by a so-called total-body counter Via the ratio of $^{59}Fe$ to $^{55}Fe$ in blood samples, also the totally absorbed amount of $^{55}Fe$ can be determined.

Subsequently, a reference solution is administered, consisting of $^{59}Fe$-labelled iron(II)sulphate and ascorbic acid at two successive breakfasts after a night's fast. No food or beverage is allowed for three hours thereafter. Another two weeks later, a new total-body measurement is made to measure the absorption of the reference dose. The reference solution is administered to make it possible to carry out corrections with regard to differences in the iron absorbing capability of the different test subjects.

The amount of $^{59}Fe$ which is added as $^{59}FeCl_3$ to the wheat-flour, isotope-labels by so-called isotopic exchange all biologically available nonheme iron (=nonblood iron) in the meals analysed, i.e. on the one hand the native iron and, on the other hand, the part of the fortification iron which is dissolved. However, that part of the fortification iron which is not dissolved in the gastrointestinal tract, is not labelled. Since the fortification iron added to the bread is labelled with another isotope ($=^{55}Fe$), the ratio of the $^{55}Fe$ portion to the $^{59}Fe$ portion as absorbed will be a direct measure of that portion of the examined, $^{55}Fe$-labelled iron compound which has been absorbed in the so-called pool of nonheme iron in the gastrointestinal tract and which thus is potentially available to absorption. This portion is a measure of the bioavailability of the examined iron compound in relation to an easily soluble iron compound, such as iron(II)sulphate. When iron(II)-sulphate is added as an iron-fortifying agent, it is, in fact, completely mixed with the pool of nonheme iron. Thus, a measure of the bioavailability in relation to a known, easily available compound is obtained, viz. the ratio of $^{55}Fe$ to $^{59}Fe$ or the relative bioavailability.

In explanation of the terminology used above, it may be mentioned that so-called heme iron which occurs in meat and blood products and is present in the form of hemoglobin and myoglobin, is a relatively small portion of the total intake of iron together with food. So-called nonheme iron which mainly occurs in bread and other cereal products, fruit and vegetables, constitutes the main part of iron in food. It may be mentioned that the composition of the meal is most important to the absorption of nonheme iron in the body.

Example 1 below accounts for the examination of bioavailability of the compound $Fe_3H_8(NH_4)(PO_4)_6 \cdot 6H_2O$ according to the invention, since this compound can be reproducibly prepared in crystalline form with very small particle size. However, the selection of this particular compound constitutes no restriction whatsoever since one of the other compounds mentioned having the formula $FeM_{3y-3}(PO_4)_y \cdot xH_2O$ could have been studied just as well.

As a comparative Example 1, an analogous examination of iron powder is described, which to date is the most frequently used type of fortification iron. Many types of iron powder have, however, very low absorbability, and only if the particle size is small enough, relatively good absorption values can be obtained. In the comparative Examples below, the absorption of so-called carbonyl iron is measured, which is considered one of the better commercial iron powders. Its particle size was 1–10 μm.

As a comparative Example 2, an analogous examination of common iron(III)phosphate is described.

Since a complete bioavailability test on humans is very complicated and time-consuming, the bioavailability of further compounds according to the invention has been tested schematically in solubility examinations in artificial gastric environment (Examples 2–6), the compound examined in Example 1 serving as a reference substance. Here, solubility tests for some commercially used iron(III)phosphates have also been included.

EXAMPLE 1

From flour fortified with $^{55}$Fe from the compound $Fe_3H_8(NH_4)(PO_4)_6 \cdot 6H_2O$ and with $^{59}$Fe from $FeCl_3$, buns weighing 40 g were made in the above-mentioned manner. Each bun contained 0.2 mg native iron and 2.2 mg fortification iron.

After measurements conducted in the manner described above on a test group of ten persons, the administered reference solution consisting of 10 ml 0.01M HCl containing training 3 mg $^{59}$Fe in the form of $FeSO_4$ and 30 mg ascorbic acid, the results summarised in the Table below were obtained.

TABLE 1

| Compound according to the invention | | | | | |
|---|---|---|---|---|---|
| Contents of nonheme iron | | | Absorption | | Relative bio- |
| Native (mg) | Fortification (mg) | Total (mg) | Native (%) | Fortification (%) | availability $^{55}Fe/^{59}Fe$ |
| 0.2 | 2.2 | 2.4 | 5.2 | 3.3 | 0.63 ± 0.04 |

COMPARATIVE EXAMPLE 1

From flour fortified with $^{55}$Fe from carbonyl iron and with $^{59}$Fe from $FeCl_3$, buns weighing 60 g were made in the above-mentioned manner. Each bun contained 0.4 mg native iron and 1 mg fortification iron.

After measurements conducted in the manner described above on a test group of ten persons, the administered reference solution being the same as above, the results summarised in the Table below were obtained.

TABLE II

| Carbonyl iron | | | | | |
|---|---|---|---|---|---|
| Contents of nonheme iron | | | Absorption | | Relative bio- |
| Native (mg) | Fortification (mg) | Total (mg) | Native (%) | Fortification (%) | availability $^{55}Fe/^{59}Fe$ |
| 0.4 | 1 | 1.4 | 5.6 | 1.0 | 0.20 ± 0.3 |

Figure 5:
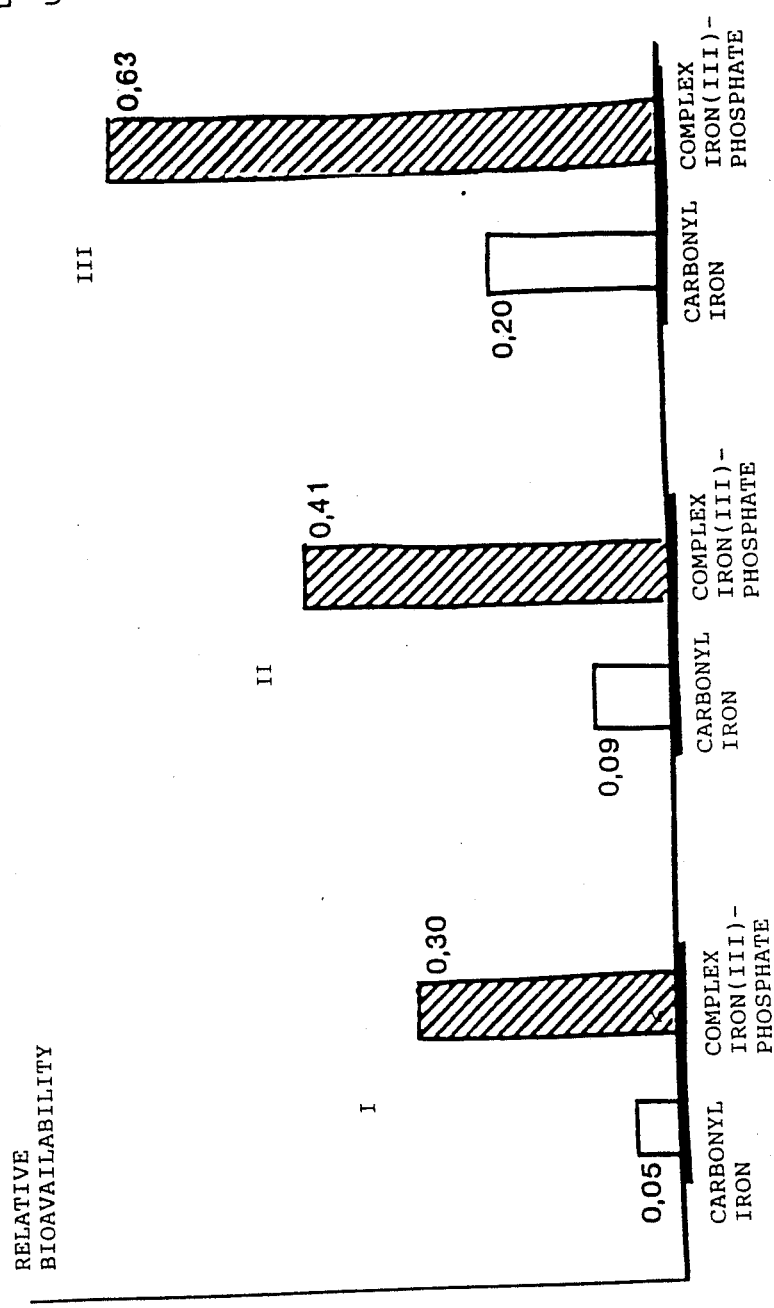

FIG. 5 is a staple diagram illustrating a comparison between the relative bioavailability of carbonyl iron and of iron-fortifying agents according to the invention when iron-fortified bread was included in different meal combinations, viz. I: broth and bread; II: breakfast with bread and milk (alternatively bread, sour milk, cereals and coffee); and III: breakfast with bread and coffee.

COMPARATIVE EXAMPLE 2

From flour fortified with $^{55}$Fe from common iron(III)phosphate and with $^{59}$Fe from $FeCl_3$, buns weighing 60 g were made in the manner stated above. Each bun contained 0.5 mg native iron and 3 mg fortification iron.

After measurements conducted in the manner described above on a test group of ten persons, the administered reference solution being the same as above, the results summarised in the Table below were obtained.

TABLE III

| Common iron(III)phosphate | | | | | |
|---|---|---|---|---|---|
| Contents of nonheme iron | | | Absorption | | Relative bio- |
| Native (mg) | Fortification (mg) | Total (mg) | Native (%) | Fortification (%) | availability $^{55}Fe/^{59}Fe$ |
| 0.5 | 3 | 3.5 | 3.6 | 1.1 | 0.31 |

It will be appreciated from the Examples above that the compound used according to the invention has a far better bioavailability than both the commercial fortifying agent which is to date most frequently used, i.e. iron powder, and the known commercial fortifying agent which, in structural respect, is its closest relation, i.e. common iron(III)phosphate. Regarding the effect on storage life, appearance and taste of the fortified food products, the three products examined are approximately equivalent.

EXAMPLES 2-6

The percentage solubility per unit of time was measured for a number of representative compounds according to the invention in artificial gastric environment (0.1M HCl; pH=1; 37° C.). The compound examined in Example 1 was also measured as a reference substance (compound A)

The compounds examined are:

Compound A: $Fe_3H_8(NH_4)(PO_4)_6 \cdot 6H_2O$
Compound B: $FeH_5Na(PO_4)_3 \cdot H_2O$
Compound C: $Fe_5H_8Na_4(PO_4)_9 \cdot 10H_2O$
Compound D: $FeH_2Na(PO_4)_2 \cdot 0.5H_2O$
Compound E: $Fe_3H_8K(PO_4)_6 \cdot 6H_2O$ It may be noted regarding compound E that structure of the compound prepared for the test did not conform entirely to the microcrystallinity of the remaining compounds, which to some extent explains its deviating solubility values.

For comparison, some iron compounds stated in Food Chemicals Codex (FCC), viz amorphous $FePO_4$ and microcrystalline $FePO_4$, were also tested in the same manner with respect to solubility.

The results are shown in Table IV below and are also graphically shown in FIG. 6.

TABLE IV

| Example No. | Compound | % Solubility | | |
|---|---|---|---|---|
| | | 10 min | 30 min | 60 min |
| 2 | A | 86 | 100 | 100 |
| 3 | B | 82 | 97 | 100 |
| 4 | C | 70 | 93 | 100 |
| 5 | D | 61 | 92 | 100 |
| 6 | E | 5 | 39 | 72 |
| Control | Amorphous $FePO_4$ | 1 | 12 | 22 |
| Control | Microcryst. $FePO_4$ | 0 | 0 | 0 |

It appears from the Table that compounds B, C and D which contain sodium, have approximately the same good solubility properties as the ammonium-containing compound A which has been tested for bioavailability. Compound E containing potassium has a low initial solubility but reached, after some time, relatively good values.

The iron phosphates known have very low values under the same test conditions The amorphous compound is the one most frequently used in connection with iron fortification, since a compound having an amorphous structure is generally more easily soluble because of its larger surface. The comparison also to the microcrystalline compound is, however, necessary since the compounds used according to the present invention are present in microcrystalline form so as to obtain a reproducible and well-defined crystal structure.

Thus, the compounds used according to the invention have surprising and highly valuable properties with respect to solubility in gastric environment.

We claim:

1. A method for iron fortification of a food product, comprising combining with the food product a complex iron (III) phosphate compound in an amount effective for providing iron fortification, said compound having the formula $$Z \cdot [FeM_{3y-3}(PO_4)_y] \cdot XH_2O$$

wherein M is $H^+$, $Na^+$, $K^+$, $NH_4^+$ or a combination thereof, $1.5 \leq y \leq 3.0$, $X \geq 0$ and Z is a positive integer, the product Z·Y being an integer, and wherein the food product comprises vegetable material, broth, or a milk-based product.

2. A method as claimed in claim 1, wherein the vegetable material comprises a grain product.

3. A method as claimed in claim 2, wherein the grain product comprises flour or flour products.

4. A method as claimed in claim 1, wherein said food product is fermented.

5. A method as claimed in claim 4, wherein said food product comprises bread.

6. A method as claimed in claim 1, wherein said food product comprises breakfast cereals.

7. A method as claimed in claim 1, wherein M comprises $H^+$ and $NH_4^+$.

8. A method as claimed in claim 1, wherein the complex iron (III) phosphate compound comprises $$Fe_3H_8(NH_4)(PO_4)_6 \cdot 6H_2O.$$

9. An iron-fortified food product, comprising vegetable material, broth, or a milk-based product and a complex iron (III) phosphate compound having the formula $$Z \cdot [FeM_{3y-3}(PO_4)_y] \cdot XH_2O$$

wherein M is $H^+$, $Na^+$, $K^+$, $NH_4^+$ or a combination thereof, $1.5 \leq y \leq 3.0$, $X \geq 0$ and Z is a positive integer, the product Z·y being an integer, said compound being present in an amount effective for providing iron fortification.

10. An iron fortified food product as claimed in claim 9, wherein the complex iron (III) phosphate compound comprises $$Fe_3H_8(NH_4)(PO_4)_6 \cdot 6H_2O.$$

11. A method for treating iron deficiency in an organism need of such treatment, comprising administering to the organism an iron fortified food product containing an effective amount of a complex iron (III) phosphate compound having the formula $$Z \cdot [FeM_{3y-3}(PO_4)_y] \cdot XH_2O$$

wherein M is $H^+$, $Na^+$, $K^+$, $NH_4^+$ or a combination thereof, $1.5 \leq y \leq 1.8$, $X \geq 0$ and Z is a positive integer, the product Z·y being an integer, and wherein the food product comprises vegetable material, broth, or a milk-based product.

12. A method for treating iron deficiency as claimed in claim 11, wherein the complex iron (III phosphate compound comprises $$Fe_3H_8(NH_4)_6 \cdot 6H_2O.$$

* * * * *